United States Patent [19]

Kriesel

[11] Patent Number: 5,236,418
[45] Date of Patent: Aug. 17, 1993

[54] FLUID MIXING AND DELIVERY APPARATUS

[75] Inventor: Marshall S. Kriesel, Bloomington, Minn.

[73] Assignee: Science Incorporated, Bloomington, Minn.

[21] Appl. No.: 986,375

[22] Filed: Dec. 7, 1992

[51] Int. Cl.$^5$ .......................................... A61M 37/00
[52] U.S. Cl. ................................................. 604/85
[58] Field of Search .............. 604/416, 249, 131, 133, 604/246, 89, 87, 88, 82, 83

[56] References Cited

U.S. PATENT DOCUMENTS

| | | |
|---|---|---|
| 3,080,866 | 12/1963 | Friedman . |
| 3,488,327 | 1/1970 | Kollinsky et al. . |
| 3,552,387 | 1/1971 | Stevens . |
| 3,563,373 | 2/1971 | Paulson . |
| 3,583,950 | 6/1971 | Kollinsky et al. . |
| 3,766,919 | 10/1973 | Cloyd . |
| 4,072,566 | 2/1978 | Lynn . |
| 4,304,705 | 12/1981 | Heilmann et al. . |
| 4,451,619 | 5/1984 | Heilmann et al. . |
| 4,485,236 | 11/1984 | Rasmussin et al. . |
| 4,539,294 | 9/1985 | Metcalfe et al. . |
| 4,639,286 | 1/1987 | Rasmussen et al. . |
| 4,713,062 | 12/1987 | Stevanato . |
| 4,737,560 | 4/1988 | Heilmann et al. . |
| 4,861,335 | 8/1989 | Reynolds . |
| 4,871,824 | 10/1989 | Heilmann et al. . |
| 4,963,367 | 10/1990 | Ecanow . |
| 4,981,933 | 1/1991 | Fazio et al. . |
| 5,013,795 | 5/1991 | Coleman et al. . |
| 5,015,373 | 5/1991 | Carr et al. . |
| 5,019,047 | 5/1991 | Kriesel ............................. 604/131 |
| 5,045,615 | 9/1991 | Heilmann et al. . |
| 5,081,197 | 1/1992 | Heilmann et al. . |
| 5,122,116 | 6/1992 | Kriesel et al. ........................ 604/89 |
| 5,147,957 | 9/1992 | Kumar . |
| 5,169,389 | 8/1992 | Kriesel . |

FOREIGN PATENT DOCUMENTS

| | | |
|---|---|---|
| 0257758A2 | 3/1988 | European Pat. Off. . |
| 0392735A2 | 10/1990 | European Pat. Off. . |
| 0392783A2 | 10/1990 | European Pat. Off. . |
| 0433034A2 | 12/1990 | European Pat. Off. . |
| 0413551A2 | 2/1991 | European Pat. Off. . |
| 0430517A2 | 6/1991 | European Pat. Off. . |
| WO8807062 | 9/1988 | PCT Int'l Appl. . |
| WO9207879 | 5/1992 | PCT Int'l Appl. . |

Primary Examiner—Gene Mancene
Assistant Examiner—Thomas Price
Attorney, Agent, or Firm—James E. Brunton

[57] ABSTRACT

An apparatus for controllably mixing separately packaged beneficial agents and parenteral fluids to form an infusible mixture and for expelling the mixture at a precisely controlled rate from a delivery subsystem which includes its own self-contained energy source and is of a compact, low profile, laminate construction. The energy source of the delivery subsystem is made up of one or more elastomeric thin film, distendable membranes each having a uniform modulus of elasticity. The membranes cooperate with a base to define a fluid chamber having a fluid outlet in communication with a dispensing port for dispensing fluid from the device. The mixing subsystem includes cooperating sterile containers, one containing a parenteral fluid, such as a diluent, and the other containing a beneficial agent such as a drug.

29 Claims, 4 Drawing Sheets

FLUID MIXING AND DELIVERY APPARATUS

BACKGROUND OF THE INVENTION

1. Field of the Invention

The present invention relates generally to fluid mixing and delivery devices. More particularly, the invention concerns an improved apparatus for mixing beneficial agents with parenteral liquids and for infusing the mixture into a patient at specific rates over extended periods of time.

2. Discussion of the Invention

Many medicinal agents require an intravenous route for administration thus bypassing the digestive system and precluding degradation by the catalytic enzymes of the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacudic agents possess a very narrow range of therapeutic effectiveness, for instance, too small a dose results in no effect, while too great a dose results in toxic reaction.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus.

Devices from which liquid is expelled from a relatively thick-walled bladder by internal stresses within the distended bladder are well known in the prior art. Such bladder, or "balloon" type devices are described in U.S. Pat. No. 3,469,578, issued to Bierman and in U.S. Pat. No. 4,318,400, issued to Perry. The devices of the aforementioned patents also disclose the use of fluid flow restrictors external of the bladder for regulating the rate of fluid flow from the bladder.

The prior art bladder type infusion devices are not without drawbacks. Generally, because of the very nature of the bladder or "balloon" configuration, the devices are unweildly and are difficult and expensive to manufacture and use. Further, the devices are somewhat unreliable and their fluid discharge rates are frequently imprecise.

A much more sophisticated fluid delivery apparatus is described in U.S. Pat. No. 5,019,047 issued to the present inventor. This device eliminates the bladder altogether and makes use of recently developed elastomeric films and similar materials, which, in cooperation with a plate-like base define a fluid chamber that contains the fluid which is to be dispensed. The elastomeric film membrane controllably forces fluid within the chamber into fluid flow channels provided in the base. In one form of the apparatus of the invention, a thin, planar shaped flow rate control member is strategically located within the chamber to precisely control the rate of flow of the liquid toward the fluid flow channels. The flow rate control member can be very thin and can be selected to have a very precise degree of permeability so that the rate of flow of fluid into the fluid flow channels can be controlled with great accuracy.

The apparatus of the present invention comprises an improvement upon the device described in the U.S. Pat. No. 5,019,047 by providing a novel means for charging the device with a mixing subsystem that includes cooperating vial assemblies, one of which contains a parenteral fluid and the other of which contains a substrate upon which an additive such as a beneficial agent is immobilized or removably affixed.

Like the earlier device, the device of the present invention uses the state-of-the-art thin membranes and films to permit the construction of compact, low profile, laminated structures which are easy to use and inexpensive to manufacture. When the devices of the invention are to be used with ambulatory patients they are constructed of flexible materials and are provided with a thin adhesive backing which permits the device to be conveniently self-affixed to the patient's arm or other parts of the body.

The device of the invention can be used for mixing virtually any type of beneficial agent such as a drug or other pharmaceutical, with a parenteral fluid such as a diluent. The drug and diluent can be separately packaged and stored until time of use. Following mixing, the device can be used to controllably infuse the mixture which may comprise antibiotics, hormones, steroids, blood anti-clotting agents, analgesics, and like medicinal agents. Similarly, the device can be used for I-V chemotherapy and can accurately deliver fluids to the patient in precisely the correct quantities and at extended microfusion rates over time.

SUMMARY OF THE INVENTION

It is an object of the present invention to provide an apparatus for controllably mixing separately packaged beneficial agents and parenteral fluids to form an infusible mixture and for expelling the mixture at a precisely controlled rate from a delivery subsystem which is of a compact, low profile, laminate construction.

It is another object of the invention to provide an apparatus of the aforementioned character which is highly reliable and easy to use by lay persons in a non-hospital environment.

Another object of the invention is to provide an apparatus in which a wide variety of beneficial agents can be controllably intermixed with a wide variety of parenteral fluids and the resulting mixture can be expeditiously used to charge the delivery subsystem.

Another object of the invention is to provide an apparatus of the character described in which fluids can be delivered either at a fixed rate or at variable rates and one which is operational in all altitudes and attitudes.

A further object of the invention is to provide a low profile, fluid delivery device of laminate construction which can be manufactured inexpensively in large volume by automated machinery.

Another object of the invention is to provide a device of the character described in which fluid is dispelled from the apparatus through either an integral infusion needle, or through a luer type connector, by a thin, distendable membrane, of membrane assemblage cooperatively associated with a thin, plate-like base.

Another object of the invention is to provide an apparatus of the aforementioned character in which the distendable member is permeable to gases at least in one direction, whereby gases within the medicinal agent can be released from the fluid chamber and not injected into the patient.

Another object of the invention is to provide a fluid delivery device embodying an iostropic distendable membrane with a uniform modulus of elasticity which cooperates with a base to define a fluid chamber having a fluid outlet in communication with a dispensing port for dispensing fluid from the device.

A further object of the invention is to provide a fluid delivery device embodying a distendable membrane assembly which cooperates with a base to define a fluid chamber having a fluid outlet in which the distendable membrane assembly is of multilaminate construction being made up of a plurality of individual members or layers which cooperate to controllably urge fluid within the fluid chamber outwardly of the fluid outlet of the delivery subsystem.

Another object of the invention is to provide an apparatus of the character described in the preceding paragraphs which enables a wide variety of beneficial agents such as drugs, pharmaceuticals, hormones and the like to be safely stored in sealed containers until time of use. The agents can then be mixed in a totally sterile environment with a suitable parenteral fluid, expeditiously introduced into the delivery subsystem and then controllably dispelled at a precise rate.

DESCRIPTION OF THE INVENTION

Referring to the drawings and particularly to FIGS. 1 through 7, there is illustrated one embodiment of the apparatus of the invention for use in mixing an additive, such as a beneficial agent with a parenteral fluid, such as a diluent, to form an infusible mixture. Following controlled mixing of the additive and the parenteral fluid, the mixture thus formed is expelled from the apparatus at a controlled rate by an internally disposed, self-contained energy source.

Figures 1, 2, 6, 7:
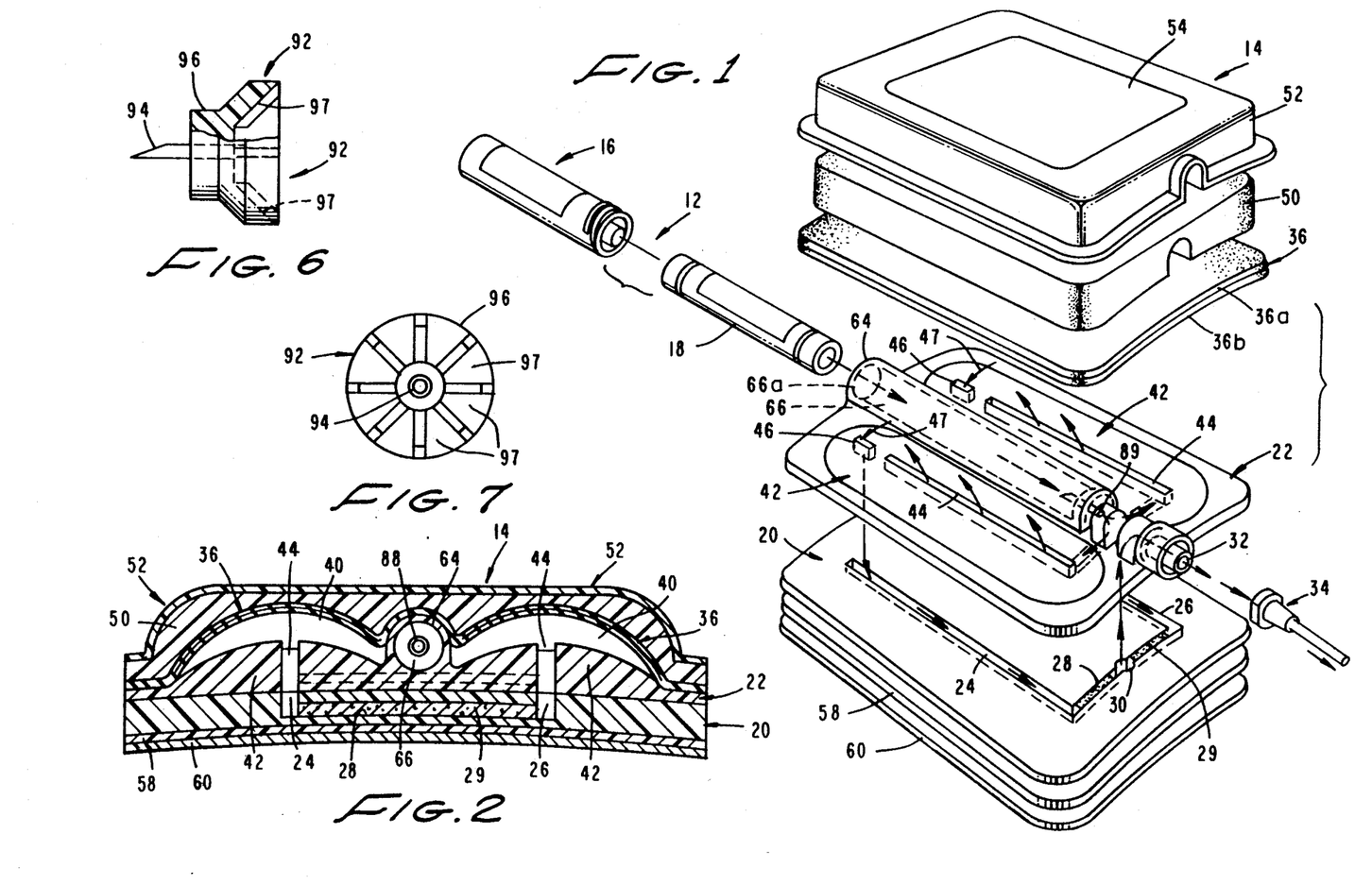
FIG. 1 is a generally perspective, exploded view of one form of the mixing and dispensing apparatus of the invention.
FIG. 2 is a cross-sectional view of the delivery subsystem of the apparatus.
FIG. 6 is an enlarged view partly in cross section of the needle holding cap provided at the inlet of the beneficial agent mixing chamber.
FIG. 7 is an end view of the needle holding cap showing the configuration of the fluid inlet flow channels provided therein.

As indicated in FIG. 1, the apparatus comprises a mixing subsystem 12 and a cooperating delivery subsystem 14. The mixing subsystem, which will presently be described in greater detail, includes a first vial assembly 16 for sealably containing the parenteral fluid and a second vial assembly 18 for sealably containing the additive to be mixed with the parenteral fluid.

The delivery subsystem of this form of the invention comprises a base made up of a first, generally planar member 20 and a second cooperating member 22. Member 22 includes a pair of longitudinally extending flow channels 24 and 26 which communicate with a transversely extending flow channel 28. Channel 28 is, in turn, in communication with a fluid outlet 30 which can be interconnected with a fluid dispensing means shown here as including a fluid dispensing port 32 and a luer fitting and delivery cannula 34.

A thin, generally planar distendable elastomeric laminate 36 cooperates with base 22 to form a pair of fluid chambers or reservoirs 40 (FIG. 2). Laminate 36 which comprises the self-contained energy source of this form of the invention is here made up of thin elastomeric members 36a and 36b. Laminate 36 is distendable out of plane in the manner shown in FIG. 2 by the introduction of fluid into the chambers under pressure. As the laminate is distended by the fluid pressure, internal stresses are formed therein which continuously urge the laminate assemblage to return toward its original planar configuration. The method of introduction of fluids into chamber 40 to controllably distend the laminate assemblage will presently be described.

Formed on base member 22 are ullage creting means, here shown as a pair of longitudinally extending, spaced apart upstanding protuberances 42. Each of the protuberances 42 is provided with a longitudinally extending first, or inlet, fluid passageway 44 and a pair of outlet ports, or passageways 46. When the apparatus is assembled in the manner shown in FIG. 2, passageways 46 are superimposed over channels 24 and 26 and protuberances 42 extend upwardly into the fluid chambers so as to provide ullage "U" within the chambers or reservoirs 40. With this construction, as distendable laminate 36 attempts to return to its original less distended, planar configuration (FIG. 1), it will move toward engagement with the upper surfaces of protuberances 42 and in so doing will controllably force the fluid contained within the fluid reservoirs 40 downwardly through passageways 46 and then into flow channels 24 and 26 in the manner indicated by the arrows 47 in FIG. 1.

The configuration of protuberances 42 ensure that all of the fluid within the reservoirs will be dispelled therefrom as the membrane returns toward its starting configuration. The interaction between the distendable membranes and the ullage protuberances is more fully described in U.S. Pat. No. 5,019,047 as is the nature of the materials used in the construction of the membranes 36a and 36b and base members 22 and 20. Accordingly, U.S. Pat. No. 5,019,047 is incorporated herein by reference as though fully set forth herein.

By constructing the laminate assemblage 36, or stored energy means, from a composite of two or more distinct elements or layers, the elastic characteristics of the stored energy means can be precisely tailored and the stored energy means can be uniquely constructed to function also as a gas permeability valve as well as the means for expelling fluids from the fluid reservoir. This unique, multilayered or gradient construction permits venting to atmosphere through the membrane surface certain selected, entrained gases or vapors in the reservoir while simultaneously substantially precluding any negative migration of selected atmospheric gases or vapors into the reservoir. Where the composite is made up of two or more layers of alternating thickness and permeability, and the permeability constants of the individual film layers are pressure dependent, the permeability of the stored energy means is effected and the direction of flow of the permiant through the membrane wall is controlled by the order in which the individual layers or gradations of the composite are assembled. The selective arrangement of the different films each with its own individual permeability constants in ascending order, will dictate the direction of flow of selected gases and vapors through the stored energy means.

The elastomeric membranes or films which make up the stored energy source can comprise rubbers, plastics and other elastomers. These include latex rubber, polyisoprene (natural rubber), butyl rubber, nitrile rubber, silicones, other homopolymer, copolymers (random, alternating, block, graft, crosslink and starblock), mechanical poly-blends and interpenetrating polymer networks.

Examples of materials found particularly well suited for this application include; silicone polymers (polysiloxanes) (high performance silicone elastomers made from high molecular weight polymers with appropriate fillers added). These materials are castable into thin film membranes and have high permeability which allows maximum transport of vapor and gas), high bond and tear strength and excellent low temperature flexibility and radiation resistance. Additionally, silicone elastomers retain their properties over a wide range of temperature ($-80°$ to $200°$ C.) are stable at high temperatures, and exhibit tensile strengths up to 2,000 lb./in elongation up to 600%.

Further, silicone (polyorganosiloxanes) are thermally stable, hydrophobic organometallic polymers with the lowest P-P interaction of all commercially available polymers. This fact coupled with the flexibility of the backbone results in a low Tg ($-80°$ C.) and an amorphous rubbery structure for the high modular weight (polydimethylsiloxanes). Silicone rubber membranes are considerably more permeable to gases than membranes of any other polymer. Depending on the medicinal fluid used and the filling and the storage mode, which will determine the desired mass transport characteristics of the membrane (permeability and selectivity), other materials of choice include polyurethanepolysiloxane copolymers, blends and IPNs. By example, polydimethylsiloxane (PDMS) and polyurethane (PU) multicomponent IPN containing 10%-20% weight of PU shows enhanced initial modulus relative to that of PDMS itself.

Interpenetrating polymer networks (IPNS) are unique blends of cross-linked polymers containing essentially no covalent bonds, or grafts between them. True IPNS are also homogeneous mixtures of component polymers. Further examples of an additional candidate materials would be a polyurethane-polysiloxane (IPN) bilaminated with a polyparaxylene or alternately bilamination of polydimethylsiloxane (PDMS) and polyparaxylene. Coextruded laminates of this type can be selected according to the desired gas permeability for vapor and $O_2$, $N_2$ and $CO_2$ diffusion and their specific selectivity requirements as well as for direction of gas migration when appropriately layered.

Manufacturers of materials suitable for use in the construction of the distendable membrane, include Dow Chemical, General Electric, B.P. Polymers, Mobay Chemical, Shell Oil Corp., Petrarch Systems, DuPont, Concept Polymers and Union Carbide Corp.

Superimposed over base member 22 and distendable laminate 36 is a porous laminate engaging body 50 and a plastic cover 52 which functions to provide a superstructure and a venting means for venting gases, if any, contained within the parenteral fluid. Affixed to the top of cover 52 is a medicant and use instruction label 54 which can be used to identify the medicinal fluid contained within the reservoirs of the device.

Affixed to the bottom of base member 20 is a cushioning means or pad 58 having adhesive on both sides. A peel strip 60 is connected to the lower surface of pad 58. For certain applications, a thin protective film may be affixed over cover 52 to prevent ingress of liquids or other contaminates into the device.

An important feature of the present embodiment of the invention comprises the unique filling means which enables chambers 40 to be filled with a precisely constituted infusible mixture which is produced using the highly novel previously identified mixing subsystem 12. To accomplish filling of the chambers 40, base member 22 here includes an upstanding longitudinally extending portion 64 having a fluid passageway 66 extending therethrough. The open end 66a of passageway 66 is adapted to closely receive vial assembly 18 in the manner shown in FIG. 4.

Before discussing the important mixing subsystem of the invention, the following terms require definition:

Additive—the element, compound, substance, agent, biologically active material, or other material which is to be added, all or in part, to the fluid introduced into the device of the invention.

Polymer—a chemical compound or mixture of compounds formed by polymerization and consisting essentially of repeating structural units.

Parenteral Fluid—any solution which may be delivered to a patient other than by way of the intestines, including water, saline solutions, alkalizing solutions, dextrose solutions acidifying solutions, electrolyte solutions, reagents, solvents and like aqueous solutions.

Beneficial Agents—any drug medicament, pharmaceutical, medical polymer, enzyme, hormone, antibody, element, chemical compound or other material useful in the diagnosis, cure, mitigation, treatment or prevention of disease and for the maintenance of the good health of the patient.

Biologically Active Material—a substance which is biochemically, immunochemically, physiologically, or pharmaceutically active or reactive. Biologically active material includes at least one or more of the following: biochemical compounds (such as amino acids, carbohydrates, lipids, nucleic acids, proteins, and other biochemicals and substances which may complex or interact with biochemical compounds), such biochemical compounds biologically functioning as antibodies, antigenic substances, enzymes, cofactors, inhibitors, lectins, hormones, hormone producing cells, receptors, coagulation actors, growth enhancers, histones, peptides, vitamins, drugs, cell surface markers and toxins, among others known to those skilled in the art. Of the group of biologically active materials described, proteins are of utmost current interest because of the large molecule genetically engineered biopharmaceuticals as those species to be immobilized and congregated on the additive carriers hereinafter to be described. A discussion of the use of biomosaic polymers as carriers for biologically active materials is set forth in European Patent Application 0,430,517 A2.

Adding means—an additive and any means for presenting the additive to the fluid flowing through the fluid passageways of the fluid delivery device of the invention in a manner such that all or any part of the additive will be added to the fluid. The adding means comprises the additive and the additive presentation means which may take the form of a functional support, or carrier, an anchorage, a deposition or reaction site or an element holder with or without some type of intermediate matrix or other release composition.

Additive Presentation Means—Any means such as a scaffold, matrix functional support or substrate for presenting the additive to the fluid flowing through the device. The scaffold or functional substrate can comprise a polymer, copolymer, an inter-polymer, a ceramic, a crystal sponge, a carbon based matrix, a cellulosic, glass, plastic, biomosaic polymers, azlactone-functional polymer beads, adduct beads, carboxylate-functional polymer beads, gums, gels, filaments and like carriers.

Figure 3:
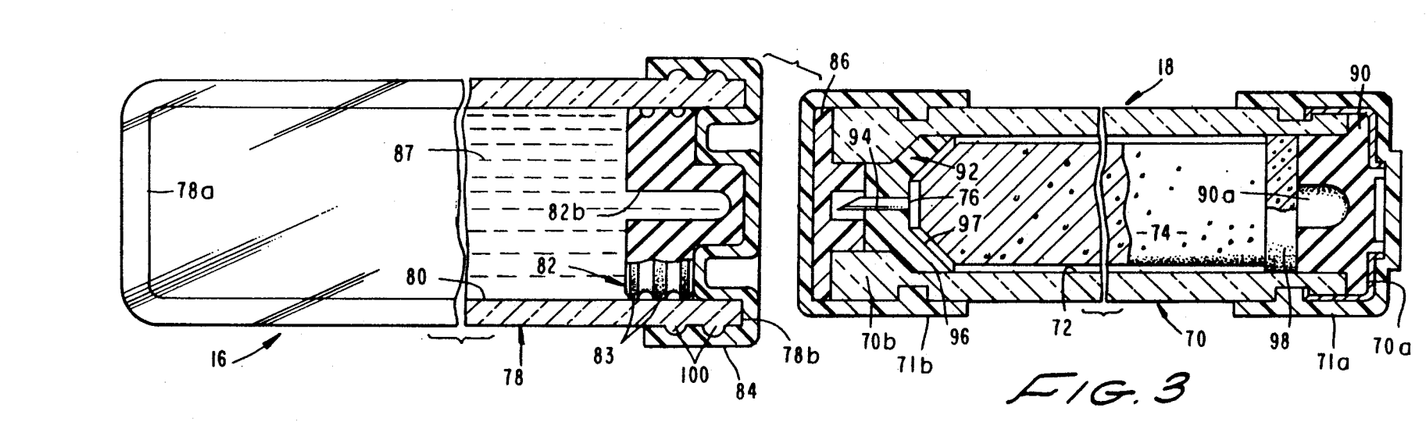
FIG. 3 is a top view of the cooperating vial assemblies of the apparatus shown partly in cross section.

Referring particularly to FIG. 3 the mixing subsystem for introducing fluid into chambers 40 of the delivery subsystem comprises a first portion shown here as a sealed cartridge 70 having an additive-containing chamber 72 for containing an additive generally designated in FIG. 3 by the numeral 74. Additive 74 can be any material of the character defined in the preceding paragraphs and, for certain applications, can be removably interconnected with a substrate or other additive presentation means of the character herein defined. Cartridge 70 has first and second ends 70a and 70b which are sealed by removable, tear-type plastic caps or covers 71a and 71b. Second end 70b is provided with a fluid inlet 76 which is in communication with chamber 72 (see FIG. 5). Cartridge 70 can be a glass vial or any other suitable sterile container for housing the additive.

Also forming a part of the mixing subsystem of the present embodiment of the invention is a second portion shown here as a fluid container 78 which is connected with first portion or cartridge 70. Container 78, which may be a glass vial, includes a fluid reservoir 80 for containing the liquid component or parenteral fluid as defined herein. During the mixing step, fluid container 78 is telescopically receivable over cartridge 70 in the manner shown in FIGS. 5 and 8. In the present form of the invention, reservoir 80 is closed by a penetrable piston 82 which is telescopically movable within fluid container 78 from a first forward position shown in FIG. 3 to a rearward position proximate the closed end 78a of container 78. Piston 82 is provided with a plurality of circumferentially extending sealing beads 83 which sealably engage the inner walls of container 78 as the piston moves rearwardly of reservoir 80.

A tear-away-type removable cover 84 encapsulates the forward faces of piston 82 and, in the manner shown in FIG. 3, sealably closes end 78b of the fluid container. After container 78 has been filled with a suitable first component such as a parenteral fluid 87, piston 82 is inserted into the open end of the container and sealing cap 84 is emplaced over the assemblage thus formed so as to maintain the first component in a sterile, sealed condition until time of use.

Figure 4:
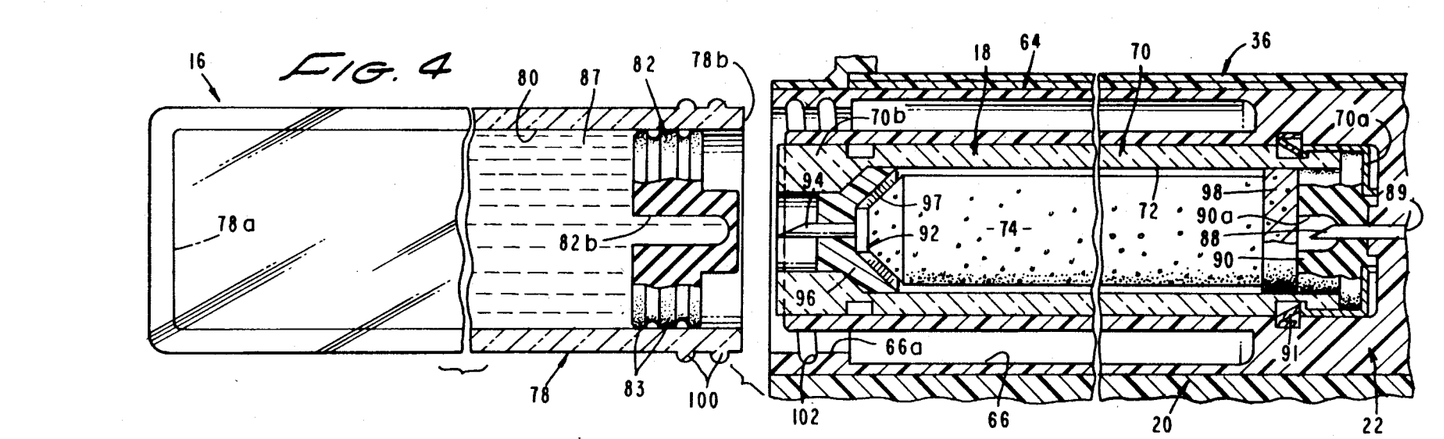
FIG. 4 is a view, partly in cross section, which is similar to FIG. 3, but showing the closure caps of the vials removed and the vials in position to be mateably interconnected.

Turning now to FIGS. 1 and 4, it is to be noted that base member 22 is provided with first flow means for establishing fluid communication between the fluid inlet 89 of the base and chamber 72 of cartridge 70, when the cartridge is positioned within the base in a manner presently to be described. As best seen in FIG. 1, inlet 89 is in communication with the inlet channels 44 provided in protuberances 42 so that fluids introduced through inlet 89 will flow into channels 44 and impinge upon distendable laminate 36 so as to move it into its distended configuration thereby forming an energy source to later controllably expel fluid from the delivery subsystem. In the form of the invention shown in FIG. 1, the first flow means comprises an inlet defining hollow needle 88 which is adapted to penetrate a penetrable plug 90 that closes first end 70a of cartridge assembly 70.

Figure 5:
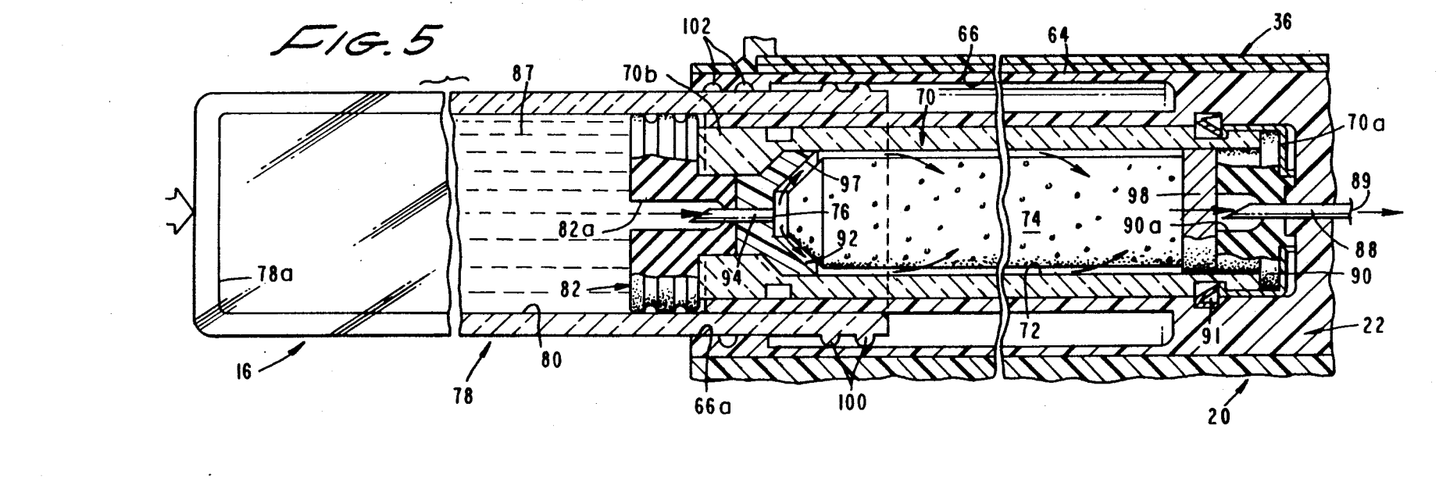
FIG. 5 is a cross-sectional view similar to FIG. 4 but showing the vials in a mated relationship for mixing of the beneficial agent with the parenteral liquid.

Provided proximate second end 70b of the cartridge assembly is second flow means for establishing fluid communication between chamber 72 of the cartridge and reservoir 80 of the fluid container upon movement of the fluid container from the first position shown in FIG. 4 to the second position shown in FIG. 5. In the present embodiment of the invention, this second flow means is provided in the form of a hollow needle assembly 92 which includes a hollow needle 94. Turning to FIGS. 6 and 7, it can be seen that hollow needle assembly 92 also includes a housing 96 which supports hollow needle 94. As best seen in FIG. 7, housing 96 includes a plurality of angularly outwardly extending fluid flow channels 97 (FIG. 7). Body 96 is receivable within chamber 72 in the manner shown in FIG. 4 and is positioned so that hollow needle 94 extends outwardly of end 70b of cartridge 70. With this construction, fluid flowing inwardly through hollow needle 94 will be distributed outwardly through flow channels 97 and into the peripheral portion of chamber 72 so that the fluid entering the chamber will flow around, about and through the additive 74 in the manner indicated by the arrows in FIG. 5.

In using the apparatus of the invention, caps 71a and 71b of the cartridge assembly are first removed in the manner shown in FIG. 4. The cartridge assembly is then inserted into open end 66a of passageway 66 formed in longitudinally extending portion 64 of base member 22. Inward pressure exerted against the cartridge subassembly will cause hollow needle 88 of the base assembly to penetrate penetrable plug 90 of the cartridge assembly in the manner shown in FIG. 4. Annular shaped locking clip 91 (FIG. 4) functions to lock the cartridge assembly in place within chamber 72. Plug 90 is provided with a central cavity 90a into which the end of needle 88 extends so that the passageway of needle 88 is in communication with internal chamber 72 which contains the additive. With this construction, fluid flowing through and about the additive 74 in the manner shown by the arrows in FIG. 5 will flow through a hydorphilic interface plug 98 which is disposed between additive 74 and plug 90 and then into the central passageway of needle 88 where it enters inlet 89 of base member 22. Plug 98 can be constructed from any suitable porous inert material and can be specially formed to control residence time of the fluid by providing any desired impedence to fluid flow toward inlet 87.

With the cartridge assembly positioned within passageway 66 of base member 22 in the manner shown in FIG. 4, tear-away cap 84 of the fluid container assembly is removed and threads 100 provided on the outer wall of vial 78 are moved into threaded engagement with internal threads 102 provided within open end 66a of passageway 66. Rotation of fluid container 78 will then cause needle 94 to penetrate penetrable piston 82 so that the outboard end of needle 94 will extend into a central bore 82a provided in piston 82. This will open a fluid flow path between reservoir 80 of container 78 and internal chamber 72 of cartridge 70. A continued urging of the fluid container 78 to the right as viewed in FIG. 5 will cause the parenteral fluid 87 contained within the fluid container to be forced through hollow needle 94 into passageways 97 of the needle holding assembly 96, into chamber 72 and around, about and through the additive materials 74 contained within the internal chamber of the cartridge 70. As the parenteral fluid flows around, about and through the additive material, the additive material will be controllably mixed with the parenteral fluid to form an infusible mixture. This mixture will then pass through hydrophilic interface plug 98 and into the fluid passageway of needle 88. The mixture flowing through needle 88 will be directed into inlet 87 of base 22, then upwardly through flow channels 44, and finally into pressural engagement with laminate assemblage 36. As the mixture flows under pressure through channels 44, it will distend laminate assembly 36 and move the central portions thereof outwardly into engagement with the longitudinally extending recesses formed in body 50 (FIG. 2). This outward distention of laminate 36 will cause the build-up of internal stresses within the laminate tending to continuously return it toward its non-distended configuration. When the outlet 32 of the delivery subsystem is open for fluid flow, membrane assembly 36 will function as the energy source to force the infusible mixture contained within chambers 40 outwardly of the chambers through fluid outlets 46 of base member 22 and into channels 24 and 26 of base member 20. The fluid mixture will then flow into transfer channel 28, through flow rate control means for controlling the rate of fluid flow through channel 28 and thence outwardly through outlet 32 and into luer connector assembly 34. The flow rate control means is here provided as a porous, permeable media 29 (FIG. 2).

Figure 8:
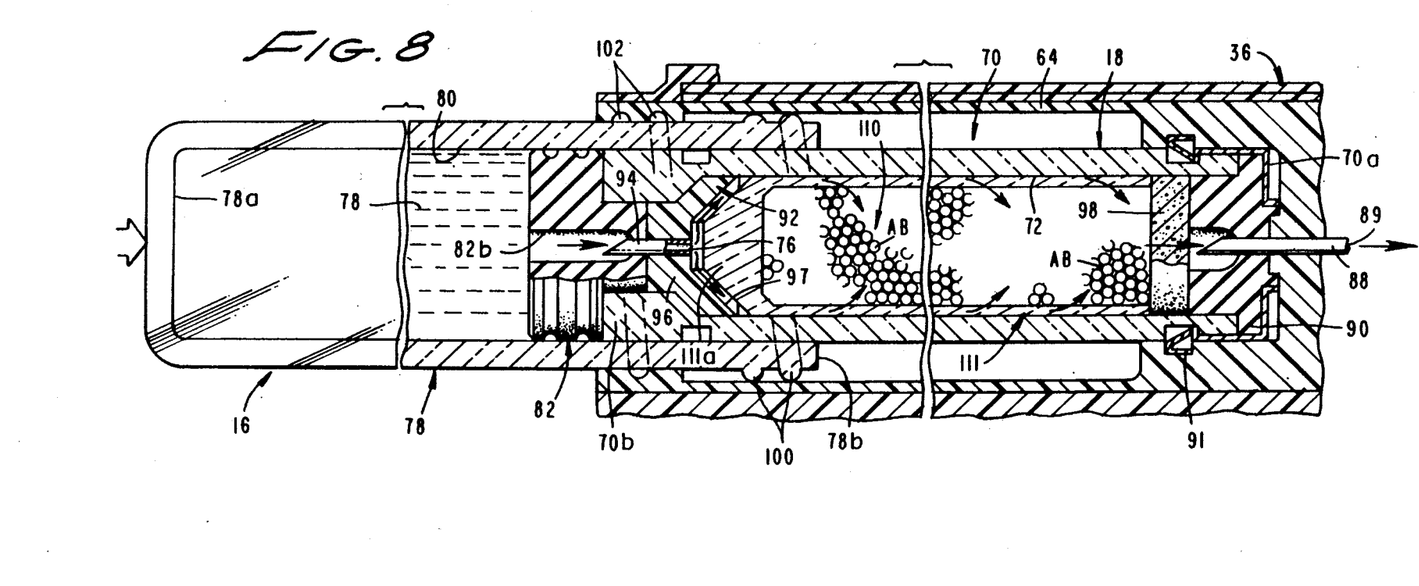
FIG. 8 is a cross-sectional view similar to FIG. 5 but showing an alternate form of beneficial agent containing vial assembly.

Turning now to FIG. 8, a slightly different form of the invention is there shown. The apparatus itself is virtually identical to that previously described and like numerals have been used in FIG. 8 to identify like components. The major difference in the embodiment of the invention shown in FIG. 8 resides in the form of the additive which is generally designated by the numeral 110. The additive here comprises an azlactone functional compound in the form of a multiplicity of azlactone beads AB which are disposed internally of a generally tubular-shaped, porous-glass frit assembly 111. Assembly 111, which includes a conically shaped forward portion 111a, is closely received within chamber 72 in the manner shown in FIG. 8. Portion 111a mates with needle assembly 92 to provide stability to the frit assembly.

Figure 9:
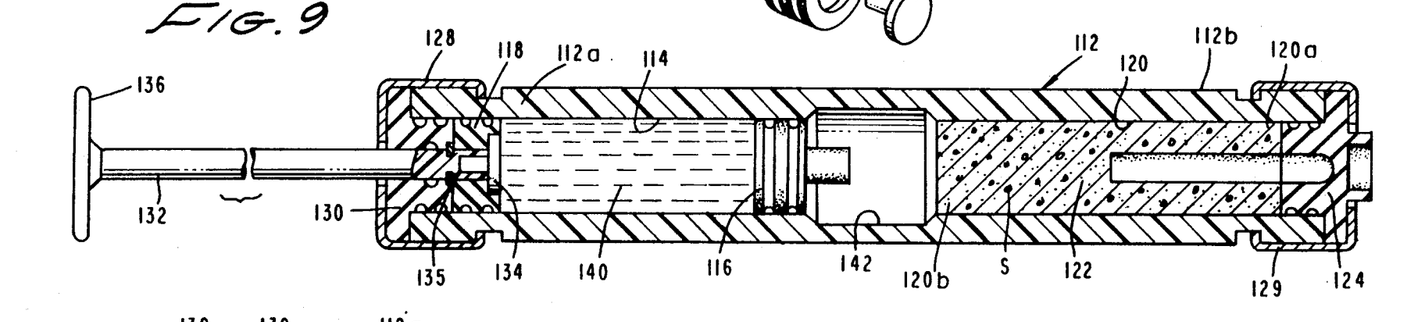
FIG. 9 is a cross-sectional view of another form of mixing and delivery apparatus of the invention.
Figure 10:
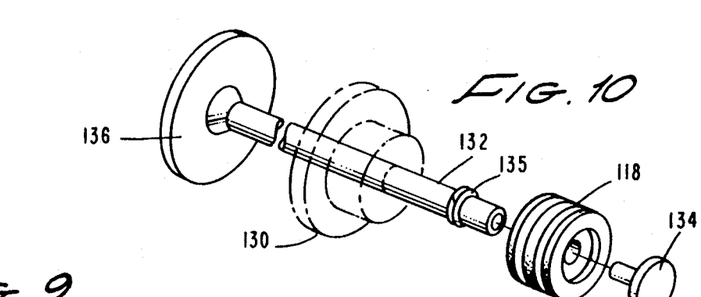
FIG. 10 is an exploded view of the plunger subassembly of the apparatus shown in FIG. 9.
Figure 11:
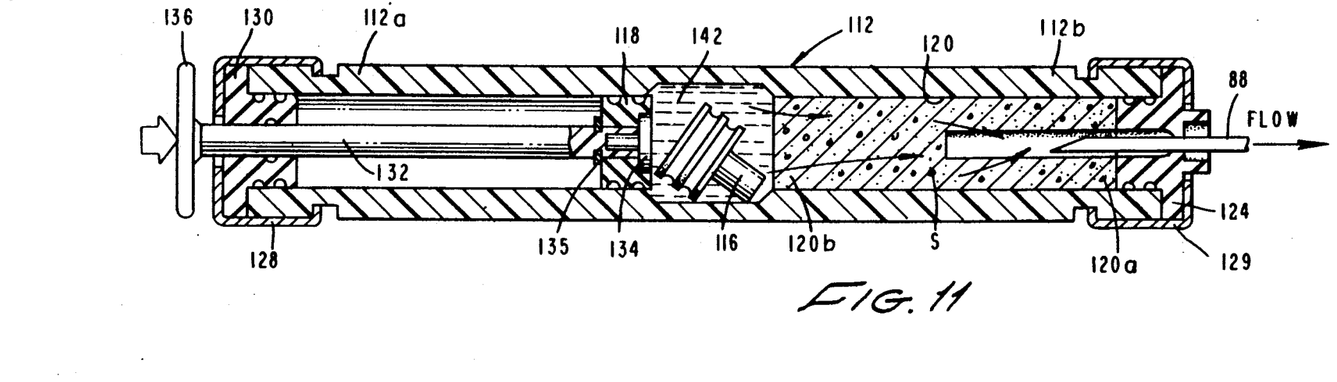
FIG. 11 is a cross-sectional view similar to FIG. 9 but showing the plunger assembly in a forward position.

Turning now to FIGS. 9 through 11, another form of the apparatus of the present invention is there illustrated. This form of the apparatus is similar in many respects to the earlier described embodiments; and in point of fact, the delivery subsystem of this form of the invention is identical to that previously described herein. This latest form of the invention makes use of a slightly different type of mixing subsystem, the construction of which is illustrated in FIGS. 9 through 11. More particularly, the mixing subsystem of this form of the invention comprises an elongated housing 112 having first and second portion 112a and 112b. First portion, 112a, includes a reservoir 114 for containing a liquid component such as a parenteral fluid. Also comprising a part of the first portion of the housing are first and second telescopically movable pistons 116 and 118 respectively. Both pistons 116 and 118 are movable from a first position shown in FIG. 9 to a second position shown in FIG. 11.

Second portion 112b of housing 112 is receivable within passageway 66 formed in longitudinally upstanding member 64 which comprises a part of base 22 (FIG. 1). Second portion 112b includes a second chamber 120 containing a beneficial agent generally designated in FIG. 9 by the numeral 122. Second chamber 120 has first and second ends 120a and 120b. First end 120a is closed by a penetrable plug 124 which closes the second end of the second chamber and is penetrable by hollow needle 88 of the base assembly of the delivery subsystem of the apparatus (see FIGS. 1 and 4). The second end 120b of second chamber 120 is adapted to communicate with reservoir 114 of the first portion of the mixing subassembly upon movement of the first and second pistons from the position shown in FIG. 9 to the position shown in FIG. 11. As shown in FIG. 11, when the first and second pistons are in the second position, fluid contained within reservoir 114 will be free to flow into second chamber 120 of the second portion of the subsystem.

As indicated in FIG. 11, when the second portion of housing 112 is inserted into passageway 66 of the base assembly, needle 88 will penetrate penetrable plug 124 in the manner indicated in FIG. 11. Needle 88 having penetrated penetrable plug 124 is in position to receive fluid flowing from reservoir 114, past plug 116, and into through, around and about additive 122. As the fluid within reservoir 114 flows around, about and through additive presentation 122, it will be mixed with the additive to form the infusible mixture which is directed into hollow needle 88. As before, fluid flowing through hollow needle 88 will flow into inlet 89 of the base assembly into channels 44 and outwardly into engagement with the membrane assemblage in a manner to urge the membrane assemblage into a distended stressed configuration. Upon opening of outlet port 32, the fluid contained within the chambers or reservoir of the housing assembly will be forced downwardly through outlet ports 46 into the channels 24 and 26 and thence into transverse channel 28. The fluid flowing through channel 28 and porous rate control media 29, will flow through outlet 32 of the housing assembly and into luer assembly 34 in the same manner as previously described herein.

Referring again to FIG. 9, it is to be noted that housing 112 is sealed at both ends by retention Caps 128 and 129. Sealing cap 128 encapsulates plunger means that is provided as a part of the first portion of housing 112. The plunger means connected to first piston 118 and functions to move the first piston from the first position shown in FIG. 9 toward the second position shown in FIG. 11. The plunger means here comprises a packing 130 which sealably closes the end of housing 112 opposite from the end sealed by penetrable plug 124. Reciprocally movable within packing 130 is an elongated shaft 132, one end of which is interconnected with piston 118 by means of connector elements 134 and 135, the latter being a snap ring receivable over shaft 132. Provided at the opposite end of shaft 132 is a disc-like handle member 136 which is gripped by the user to manually move piston 118 from the first position shown in FIG. 9 to the second position shown in FIG. 11. As piston 118 moves toward the second position, pressure will be exerted on the parenteral fluid 140 contained within chamber 114 Fluid under pressure will impinge upon piston 116 and, upon reaching a predetermined level, will urge piston 116 to the right causing it to fall into an enlarged diameter intermediate chamber 142 which is disposed between reservoir 114 and second chamber 120 of housing 112. When piston 116 falls into intermediate chamber 142, the parenteral fluid which was contained within reservoir 114 will be forced in the direction of the arrows of FIG. 11 into second chamber 120 and will flow around, about and through the additive presentation means 122 in the manner indicated in FIG. 11.

As before the additive removably affixed to the additive presentation means 122 can be any form of beneficial agent identified in the preceding definitional paragraphs including any biologically active material. In the form of the invention shown in the drawings, the additive is removably connected to an additive presentation means here shown as a porous scaffold S to which the additive is removably affixed. Porous scaffold S may take on various physical configurations including a porous ceramic, a porous polymer matrix, a crystal sponge, or a functional polymer.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A mixing and fluid delivery apparatus comprising:
   (a) fluid delivery subsystem comprising:
      (i) a base having a fluid inlet and fluid outlet interconnected by a fluid flow path; and
      (ii) a distendable membrane constructed of an elastic material which is fitted over said base to define an internal chamber in communication with said fluid inlet and said fluid outlet, said membrane being distendable by fluid introduced into said internal chamber under pressure through said fluid inlet, said membrane having a tendency to return to a substantially nondistended configuration whereby fluid within said internal chamber will be expelled through said fluid outlet; and
   (b) a mixing subsystem interconnectable with said fluid delivery subsystem for introducing fluid into said internal chamber thereof under pressure, said mixing subsystem comprising:
      (i) a first portion having an additive containing chamber for containing a first component comprising an additive, said first portion having first and second ends; and
      (ii) a second portion having a reservoir containing a second component, said first and second portions being interconnectable to permit fluid flow between said reservoir containing said second component and said additive-containing chamber.

2. An apparatus as defined in claim 1 in which said second component comprises a liquid and in which said base includes first flow means for establishing fluid communication between said fluid inlet of said base and said additive-containing chamber of said cartridge.

3. An apparatus as defined in claim 1 in which said first portion includes second flow means for establishing fluid communication between said additive-containing chamber and said reservoir of said fluid container.

4. An apparatus as defined in claim 3 in which said first end of said first portion is sealed by a penetrable plug and in which said first flow means comprises a hollow needle adapted to penetrate said penetrable plug.

5. An apparatus as defined in claim 3 in which said reservoir of said second portion is closed by a piston movable within said second portion between first and second positions.

6. An apparatus as defined in claim 5 in which said second flow means comprises a hollow needle adapted to penetrate said piston.

7. An apparatus as defined in claim 5 in which said liquid component comprises a diluent.

8. An apparatus as defined in claim 5 further including a substrate receivable within said additive-containing chamber, said additive being removably affixed to said substrate.

9. An apparatus as defined in claim 8 in which said additive comprises a beneficial agent.

10. An apparatus as defined in claim 9 in which said beneficial agent comprises a drug.

11. A mixing and fluid delivery apparatus comprising:
    (a) fluid delivery subsystem comprising:
       (i) a base having a passageway provided with a first hollow needle, a fluid inlet in communication with said hollow needle and fluid outlet interconnected with said fluid inlet by a fluid flow path; and
       (ii) a distendable membrane laminate assembly constructed of thin membranes of elastic material which is fitted over said base to define first chamber in communication with said fluid inlet and said fluid outlet, said membrane laminate assembly being distendable by fluid introduced into said first chamber under pressure through said fluid inlet, said membrane laminate assembly having a tendency to return to a substantially nondistended configuration whereby fluid within said first chamber will be expelled through said fluid outlet; and
    (b) a mixing subsystem for introducing fluid into said chamber under pressure, said mixing subsystem comprising:
       (i) a fluid container having a reservoir containing a liquid component and a penetrable piston movable within said reservoir between a first position and a second position; and
       (ii) a cartridge assembly including a cartridge receivable within said passageway of said base and telescopically receivable within said fluid container for movement between first and second positions, said cartridge having a second chamber containing a beneficial agent and having first and second ends, said first end being closed by a penetrable plug penetrable by said first hollow needle and said second end having a second hollow needle adapted to penetrate said penetrable piston whereby, upon movement of said cartridge within said fluid container from said first position to said second position, fluid contained within said reservoir will flow into said second chamber of said cartridge and then outwardly of said second chamber into said fluid inlet of said base.

12. An apparatus as defined in claim in which said passageway of said base is provided with internal threads and said fluid container is provided with external threads mateable with said threads of said passageway of said base.

13. An apparatus as defined in claim 11 in which telescopic movement of said cartridge within said fluid container from said first position to said second position causes movement of said penetrable piston within said fluid container from said first position therewithin to said second position therewithin.

14. An apparatus as defined in claim 11 in which said cartridge assembly further includes flow control means for controlling fluid flow toward said fluid inlet of said base.

15. An apparatus as defined in claim 14 in which said flow control means comprises an interface plug disposed between said additive and said penetrable plug.

16. An apparatus as defined in claim 14 further including removable sealing means for closably sealing said cartridge assembly.

17. An apparatus as defined in claim 14 further including removable sealing means for closably sealing said fluid container.

18. An apparatus as defined in claim 14 further including a substrate receivable within said chamber of said cartridge, said additive being removably affixed to said substrate.

19. An apparatus as defined in claim 18 in which said substrate comprises a porous body.

20. An apparatus as defined in claim 18 in which said substrate comprises a gel, said additive being intermixed with said gel.

21. An apparatus as defined in claim 18 in which said substrate comprises an azlactone functional polymer.

22. An apparatus as defined in claim 18 in which said substrate comprises a functional polymer.

23. A mixing and fluid delivery apparatus comprising:
    (a) fluid delivery subsystem comprising:
        (i) a base having a passageway provided with a first hollow needle, a fluid inlet in communication with said hollow needle and fluid outlet interconnected with said fluid inlet by a fluid flow path; and
        (ii) a distendable membrane constructed of elastic material which is fitted over said base to define first chamber in communication with said fluid inlet and said fluid outlet, said membrane being distendable by fluid introduced into said first chamber under pressure through said fluid inlet, said membrane having a tendency to return to a substantially nondistended configuration whereby fluid within said first chamber will be expelled through said fluid outlet; and
    (b) a mixing subsystem interconnected with said fluid delivery subsystem for introducing fluid into said chamber under pressure, said mixing subsystem comprising an elongated housing having:
        (i) a first portion including a reservoir containing a liquid component and first and second telescopically movable pistons, each movable between a first position and a second position; and
        (ii) a second portion receivable within said passageway of said base, said second portion having a second chamber containing a beneficial agent and having first and second ends, said first end being closed by a penetrable plug penetrable by said first hollow needle upon interconnection of said mixing subsystem in the said delivery subsystem and said second end being in communication with said reservoir of said first portion upon movement of said first and second pistons from said first position to said second position, whereby fluid contained within said reservoir of said first portion will flow into said second chamber of said second portion and then outwardly of said second chamber into said fluid inlet of said base.

24. An apparatus as defined in claim 23 in which said passageway of said elongate housing is provided with an intermediate chamber disposed between said reservoir and said second chamber, said second piston being movable into said intermediate chamber upon movement of said first piston toward said second position.

25. An apparatus as defined in claim 24 in which said first portion of said housing includes a plunger means connected to said first piston for moving said first piston toward said second position.

26. An apparatus as defined in claim 25 in which said plunger means comprises a packing disposed at one end of said reservoir and a shaft sealably movable within said packing, said shaft being connected to said first piston.

27. An apparatus as defined in claim 26 further including sealing means for closably sealing both ends of said elongate housing assembly.

28. An apparatus as defined in claim 27 further including a substrate receivable within said second chamber of said second portion, said additive being removably affixed to said substrate.

29. An apparatus as defined in claim 26 in which said substrate comprises a porous body.

* * * * *